(12) United States Patent
Kodera et al.

(10) Patent No.: US 6,455,273 B1
(45) Date of Patent: Sep. 24, 2002

(54) METHOD FOR PRODUCING A PROTEIN HYDROLYSATE WITH LOW BITTERNESS

(75) Inventors: Tomohiro Kodera; Minao Asano; Tetsuay Miwa; Noriki Nio, all of Kanagawa-ken (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/805,248

(22) Filed: Mar. 14, 2001

(51) Int. Cl.[7] .................. C12P 21/06; A23L 1/211; A23L 1/31; A23K 1/00; A23C 9/12
(52) U.S. Cl. .................. 435/68.1; 426/52; 426/56; 426/63; 426/46; 435/68.1
(58) Field of Search .................. 435/68.1; 426/46, 426/52, 56, 63

(56) References Cited

U.S. PATENT DOCUMENTS 5,824,534 A  * 10/1998  Asano et al.

FOREIGN PATENT DOCUMENTS

| EP | 1036843 A | * | 9/2000 |
| JP | 60098993 A | * | 6/1985 |
| JP | 60192599 A | * | 10/1985 |
| JP | 8-264 | | 1/1996 |
| JP | 9-121870 | | 5/1997 |
| JP | 09121870 A | * | 5/1997 |
| JP | 200083695 A | * | 3/2000 |

OTHER PUBLICATIONS

Asano et al. Characterization of novel cysteine proteases from germinating cotyledons of soybean [glycine max (I.) merrill] (Aug. 1999) J. Biochem., vol. 126, pp. 296–301.*

Kawai et al., Characterization of 30–kDa fragments derived from β–conglycinin degradation process during germination and seedling growth of soybean (1997) Biosci. Biotech. Biochem., vol. 61, No. 5, pp. 794–799.*

* cited by examiner

*Primary Examiner*—Jon P. Weber
(74) *Attorney, Agent, or Firm*—Oblon, Spivak, McClelland, Maier & Neustadt, P.C.

(57) ABSTRACT

A method for producing a protein hydrolysate with low bitterness by contacting a protein with a protease having a low specificity to cleave a site of a hydrophobic amino acid residue in the protein.

19 Claims, No Drawings

METHOD FOR PRODUCING A PROTEIN HYDROLYSATE WITH LOW BITTERNESS

BACKGROUND OF THE INVENTION

1. Field of the Invention

The present invention relates to a method for producing a protein hydrolysate with low bitterness. More specifically, the present invention relates to a method for producing a protein hydrolysate with low bitterness, by a simple procedure of enzymatic hydrolysis using a protease having a low specificity to cleave a site of a hydrophobic amino acid residue in the protein, with no further need of any procedure to reduce bitterness.

2. Discussion of the Background

Various proteases are used to modify the properties of food proteins. The resulting protein hydrolysates have various functions and properties and are used in diversified manners, depending on the purpose. For example, because the enzymatic protein hydrolysates contain less free amino acids, as compared with HVP (acid-hydrolyzed vegetable proteins) and HAP (acid-hydrolyzed animal proteins), they are used as seasoning materials, due to their mild taste and thickness. As nutrient materials, peptides are rapidly absorbed, as compared with free amino acids. In a peptide form, branched chain amino acids are also absorbed well. Furthermore, corn proteins, which are difficult to digest, can be digested and absorbed as a nutrient when hydrolyzed to peptides. As a food material, a peptide form is superior to a protein form, because modification of proteins into peptides involves the improvement of solubility at a wide range of pH, the decrease of viscosity, the improvement of hygroscopicity and moisture, and the modification of emulsifiability, foaming potency, and gelatinizability. Furthermore, it is reported that a soybean protein hydrolysate has physiological activities, such as a hypocholesterolemic activity, inhibition of cholesterol absorption, a bile acid-binding activity, suppression of platelet aggregation, and an anti-oxidative activity. Additionally, the allergenecity of a protein is reduced or eliminated when the protein is hydrolyzed into a low molecular weight peptide composition.

As has been described above, enzymatic protein hydrolysates have such excellent functions and properties. However, they have strong bitterness. Currently, therefore, the protein hydrolysates have only limited applicability as foodstuffs. Thus, as an approach to reduce the bitterness, a method for eliminating the bitterness by using an aminopeptidase specifically cleaving the N-terminal hydrophobic amino acid residues (Japanese Patent Application, Laid-Open No. 173168/1996) has been described. However, this method disadvantageously involves an increase in free amino acids. Other methods, restricting substrate proteins, have also been reported (Japanese Patent Application, Laid-open Nos. 344847/1993 and 23863/1998), but the applicable range thereof is limited. Furthermore, the use of agents which mask bitterness (Japanese Patent Application. Laid-open Nos. 162/1997 and 100297/1997), a method by fractionating and removing peptides with bitterness (Japanese Patent Application, Laid-open No. 244978/1993), polymerization with a plastein reaction (J. Agric. Biol. Chem. 34, 1484 (1970)), and the utilization of enveloping compounds (Japanese Patent Application, Laid-open No. 283246/1990) have also been 1 g reported. However, all these methods have various problems, including a loss of essential functions of peptides, a low recovery yield, a need for specific equipment, and high cost.

Accordingly, there remains a need for a protein hydrosylate which overcomes the disadvantages discussed above.

SUMMARY OF THE INVENTION

It is an object of the present invention to provide a method for producing a protein hydrolysate with low bitterness, without the problems associated with the materials described above.

The protein hydrolysate prepared in accordance with the present invention tastes less bitter than hydrolysates prepared by enzymes used conventionally in the food industry. Accordingly, the protein hydrolysates with less free amino acid content are readily ingestible. Additionally, the essential nutrient value of the protein can sufficiently be utilized. Hence, the protein hydrolysates prepared in accordance with the invention may be used in numerous applications, such as foodstuffs, infant formulas, medicinal diets, seasonings, flavor-modifying materials, food property-modifying materials, food additives, and feeds.

Thus, the present invention relates to a method for producing a protein hydrolysate with low bitterness, comprising contacting a protein with a protease having a low specificity to cleave a site of a hydrophobic amino acid residue in the protein.

In another embodiment, the present method relates to a method for producing a protein hydrolysate with low bitterness where the protease has a specificity to cleave C-terminals of hydrophilic amino acid residues adjacent to C-terminals of hydrophobic amino acid residues in the protein.

In another embodiment, the present method relates to a method for producing a protein hydrolysate with low bitterness wherein the protease is a thiol protease derived from germinating soybean cotyledons.

A more complete appreciation of the invention and many of the attendant advantages thereof will be readily obtained as the same becomes better understood by reference to the following detailed description.

DETAILED DESCRIPTION OF THE INVENTION

The present inventors have focused their attention on the mechanism by which peptides exert a bitter taste. More specifically, proteases conventionally used in the industry have a substrate specificity to selectively cleave a site of hydrophobic amino acids. Thus, hydrophobic amino acids are very likely to be present at the N-terminals and/or C-terminals of the peptides formed by the hydrolysis. Additionally, it is known that once the protein hydrolysates with such strong bitterness are treated with a peptidase specific to hydrophobic amino acid residues, the bitterness can be eliminated. Thus, the bitterness of the protein hydrolysates is considered to be due to the presence of hydrophobic amino acids at the C-terminals and/or N-terminals of the peptides contained therein.

The present inventors have discovered that a protein hydrolysate with low bitterness can be obtained with no further need of any treatment to reduce bitterness, by contacting a protein with a protease having a low specificity to cleave a site of a hydrophobic amino acid residue in the protein.

The protease having low specificity to cleave a site of a hydrophobic amino acid residue in the protein used in the present invention is one having a cleavage tendency to reduce the probability of the presence of hydrophobic amino acid residues at the C-terminals and/or N-terminals of the peptides formed by the hydrolysis. By hydrolyzing a protein using a protease having such a substrate specificity, a protein hydrolysate with less free amino acids and with weak bitterness can be obtained.

In accordance with the present invention, at least one type of protease having a low specificity to cleave a site of a hydrophobic amino acid residue in the protein is used. Furthermore, at least one type of protease having a low specificity to cleave a site of a hydrophobic amino acid residue in the protein may be used in combination with at least another type of protease having a substrate specificity to cleave a site of a hydrophobic amino acid residue in the protein, as long as the combination can comply with the purpose to provide a protein hydrolysate with low bitterness with no need of any additional process for reducing the bitterness. The proteases may satisfactorily be in the form of a crude enzyme separated from a natural origin in a purified form thereof or in an expression product of genetically recombinant organisms.

The activity of the proteases to cleave a site of a hydrophobic amino acid residue in the protein can be assayed, for example, by the following method. However, the method for estimating the activity is not limited to the method described below.

1. The enzyme is added to a peptide hormone (50 mmol) as a substrate to 0.1% by weight and is then mixed with a buffer adjusted to the optimum pH. As the peptide hormone, oxidized-form insulin B chain, neurotensin, glucagon or leutenizing hormone-releasing hormone, for example, can be used.

2. The mixture is subjected to a reaction at the optimum temperature for one hour. After the analysis of the resulting peptides, the reaction time is to be appropriately adjusted in case the reaction is too weak or too strong.

3. The reaction is terminated with formic acid. The product is separated by C18 reverse-phase column chromatography (using 0.1% TFA as the buffer A and 0.1% TFA-containing $CH_3CN$ as the buffer B, and the peptides being eluted by a 10–100% gradient of the buffer B for 45 minutes). The amino acid sequences of the separated peptides are determined by analytical methods with a protein sequencer, mass spectrometry or amino acid analyzer, for example.

4. The enzymatically cleaved sites of the substrate are determined by the methods described above. Proteases showing a degradation pattern similar to subtilisin, thermolysin, pepsin, trypsin and chymotrypsin, etc., which are known to cleave the site of hydrophobic amino acids and whose hydrolysates taste bitter are defined as enzymes with a high activity to cleave a site of a hydrophobic amino acid residue in the protein.

Preferable examples of the protease having a low specificity to cleave a site of a hydrophobic amino acid residue in the protein include cysteine protease D3 (thiol protease D3) derived from germinating soybean cotyledons (Japanese Patent Application, Laid-open No. 246/1996) and a recombinant product thereof (Japanese Patent Application, Laid-open No. 121870/1997). Each of these patent applications are incorporated herein by reference.

The enzyme D3 is a thiol protease of a molecular weight (SDS-PAGE) of 26 to 30 kDa and has a specificity to cleave C-terminals of hydrophilic amino acid residues adjacent to C-terminals of hydrophobic amino acid residues in a protein. Other characteristics of the enzyme D3 are as follows:

(1) optimum pH: about 3 to 7;
(2) optimum temperature: about 30 to 50° C.;
(3) inhibitors: trans-epoxysuccinyl-L-leucylamide(4-guanizino)-butane (E-64);
(4) activators: 2-mercaptoethanol, cysteine and reduced glutathione.

In preferred embodiments of the present invention, the thiol protease may have one or any combination of the characteristics described above.

Hydrolysis of a protein by the protease D3 having such substrate specificity can generate a protein hydrolysate with low free amino acids and low bitterness.

The substrate protein to be used in the present invention is with no specific limitation. Preferable examples thereof include vegetable proteins such as soybean protein and gluten, and animal proteins such as casein, gelatin, muscle protein, globulin and albumin. Particularly, edible proteins for use as food are preferably used. According to the present invention, one type of substrate protein may be used by itself, and a mixture of different types of protein may also be used. Still further, the substrate protein may contain substances (for example, sugar. and edible dietary fiber) other than the protein, like a soy protein isolates.

The average molecular weight of peptides in the hydrolysate is determined by measuring the nitrogen level (NBD-F value) in the amino form and in the imino form with 4-nitro-7-nitrobenzo-2-oxa-1,3-diazole (NBD-F) reagent [K. Imai, Y. Watanabe, Anal. Chem. Acta., 130, 377–383 (1983)] (Japanese Patent Application, Laid-open No. 264/1994), and calculating from the NBD-F value and the concentration of the hydrolysate subjected to the analysis. Each of these publications are incorporated herein by reference.

The range of the molecular weight of the peptides in the hydrolysate is 200 to 8,000, preferably 200 to 5,000, more preferably 200 to 2,000 Da. This range includes all specific values and subranges therebetween, such as, but not limited to, 250, 300, 350, 400, 450, 500, 600 and 700 Da. Alternatively, the contents of free amino acids concurrently present in the hydrolysate obtained are preferably 10% by weight or less, more preferably 5% by weight or less.

In order to obtain such a protein hydrolysate, the protease having a low specificity to cleave a site of a hydrophobic amino acid residue in the protein is used at a concentration of 0.01 to 1 part by weight per 100 parts by weight of the protein (this range of concentration includes all specific values and subranges therebetween, such as, but not limited to 0.05, 0.1, 0.2, 0.3, 0.4, 0.5, 0.6, 0.7, 0.8 and 0.9 parts by weight per 100 parts by weight of the protein), and is subjected to a reaction at 30 to 45 ° C. (his range of temperature includes all specific values and subranges therebetween, such as, but not limited to 31, 32, 33, 34, 35, 36, 37, 38, 40 and 43° C.) for about 1 to 100 hours (this range includes all specific values and subranges therebetween, such as, but not limited to 2, 5, 10, 20, 30, 40, 50 ,60, 70, 80 and 90 hours).

The bitterness of the protein hydrolysate thus obtained is preferably 0.05% or less, more preferably 0.04% or less and most preferably 0.02% or less, based on an equivalent concentration according to the measurement of bitterness as described below.

The hydrosylate obtained by the method of the present invention may be used to produce a variety of products, such as foodstuffs, infant formulas, medicinal diets, seasonings, flavor-modifying materials, food property-modifying materials, food additives, and feeds. This is accomplished by producing a protein hydrolysate according to the inventive method and then incorporating the protein hydrolysate into the product.

EXAMPLES

Having generally described this invention, a further understanding can be obtained by reference to certain specific examples which are provided herein for purposes of illustration only, and are not intended to be limiting unless otherwise specified.

Reference Example

In the following example, six amino acid residues (Cys, Asp, Asn, Tyr, Try and Ser) were added to the C-terminal of the recombinant protease D3 described in Japanese Patent Application, Laid-open No.121870/1997, to prepare a recombinant protease D3 (referred to as "rD3" hereinafter) of a total length of 247 amino acids, which is the same as the native D3 derived from germinating soybean cotyledons. In order to increase the expression of rD3 in *Escherichia coli*, trp promoter readily inducing transcription when the host is deficient in tryptophan was used as the promoter during the production of rD3. The method for producing rD3 is described below.

1. Preparation and Culturing of Transformant and Preparation of Inclusion Body

Fresh colonies of JM 109 bacteria transformed with a plasmid integrated with the rD3 gene were inoculated in 2×YT culture medium (3 ml) containing 150 µg/ml ampicillin, and incubated at 37° C. for about 10 hours. The preculture medium (1 ml) was transferred to M9-casaminoic acid culture medium (50 ml) containing 150 µg/ml ampicillin and incubated at 37° C. for about 20 hours. After the termination of the culturing, the bacterial pellets were harvested and suspended in solution A (10 mM Tris-HCl, 1 mM EDTA, pH 8.0) and disrupted by sonication. The insoluble protein fraction (inclusion bodies) were isolated by centrifugation at 10,000 rpm for 10 minutes, and washed twice with solution B (solution A+0.5% Triton X-100) and additionally washed twice with the solution A.

2. Refolding of rD3

The inclusion bodies were resuspended in solubilization buffer (8 mM urea, 10 mM DTT, 50 mM Tris-HCl, 5 mM EDTA, pH 8.0) to a final protein concentration of about 20 mg/ml and incubated at 40° C. for one hour. After incubation, the solution was centrifuged at 10,000 rpm for 10 minutes to obtain the supernatant. The solution (2.5 ml) of the rD3 was loaded to a desalting column PD-10 (Sephadex G-25, Amersham Pharmacia Biotech) equilibrated with a renaturation buffer, followed by elution with the renaturation buffer (3.5 ml), for refolding of the rD3. The renaturation buffer was 50 mM potassium phosphate, 5 mM EDTA, 1 mM glutathione (reduced type), 0.1 mM glutathione (oxidized type), pH 10.5.

3. Activation of rD3

The refolded rD3 with the pro sequence is in a non-active form. Therefore, rD3 preliminarily activated by the following method was used for protein hydrolysis.

The refolded rD3 was mixed with 50 mM acetate buffer (pH4.0) to about 5 mg/ml, and incubated at 37° C. After the disappearance of the opaqueness, the resulting rD3, which was in an active form, was concentrated and desalted with Ultrafree (Millipore) of a fractionation molecular weight of 10 kDa. After the amount of the protein was assayed, rD3 was used for protein hydrolysis.

Example 1

Soy protein isolates solution was adjusted with hydrochloric acid to about pH 4.5. The active form rD3 was added to the solution to the substrate/enzyme ratio of 500/1 (by weight), and subjected to a reaction at 37° C. for 24 hours. After the termination of the reaction, the enzyme was inactivated with a thermal treatment at 100° C. for 15 minutes. The supernatant fraction was recovered by centrifugation. The pH in the supernatant fraction was adjusted with NaOH to about neutrality, and the hydrolysate was recovered by freeze-drying. The free amino acids concurrently present in the hydrolysate were at 5% by weight or less.

Alternatively, pepsin or alkalase (manufactured by Novo Nordisk A/S) instead of the active rD3 was added to a separated soybean protein solution, which was preliminarily adjusted to the optimum pH for each of pepsin and alkalase, to the final substrate/enzyme ratio of 500/1 (by weight), and subjected to a reaction at 37° C. for 24 hours. After the termination of the reaction, hydrolysates were recovered by the same method. The free amino acids concurrently present in the hydrolysates were at 5% by weight or less. The average molecular weights of the hydrolysates are shown in Table 1.

TABLE 1

| Enzyme | Average molecular weight |
| --- | --- |
| rD3 | 1153 |
| Pepsin | 1256 |
| Alkalase | 585 |

The bitterness of the protein hydrolysates was evaluated as follows.

The bitterness of the protein hydrolysates was estimated in aqueous solution. The bitterness was evaluated sensorially by six panelists by comparing samples to standard aqueous bitter standard. The standard for bitterness was a caffeine solution, with 0.00, 0.02, 0.04, 0.06 and 0.08% by weight. The bitterness score of each standard solution was designated as 1 (absolutely no bitterness), 2 (almost no bitterness), 3 (slight bitterness), 4 (with bitterness) and 5 (strong bitterness). The bitterness intensity was expressed as an isointensity caffeine concentration as mentioned below. All of the solutions tasted had to be beforehand neutralized and desalted, so that sour and salt tastes did not interfere with bitterness.

Then, the hydrolysates were dissolved in water to a given concentration (2% by weight in the Example), and the individual panelist compared the bitterness between the sample solutions and the standard caffeine solutions for bitterness. The score of the bitterness of a standard solution, to which the bitterness of the sample solution is closest, is defined as the bitterness score of the sample solution. The average of the scores given by the individual panelists was calculated. The caffeine concentration (equivalent concentration) corresponding to the average is designated as the indicator of the bitterness of each sample.

The equivalent concentration of each sample as obtained by the aforementioned assessment method is shown in Table 2. The hydrolysates by rD3 have significantly low bitterness, as compared with the bitterness of the other enzymatic hydrolysates. The bitterness is endurable for a food use.

TABLE 2

| Enzyme | Equivalent concentration (%) |
| --- | --- |
| rD3 | 0.020 |
| Pepsin | 0.053* |
| Alkalase | 0.067* |

*Significantly more bitter than the hydrolysate produced by rD3 at $p < 0.05$.

Example 2

A casein solution was adjusted with hydrochloric acid to about pH 4.5. In the same manner as in the case of the soy protein isolates solution, the active rD3 was added to the solution, to a final substrate/enzyme ratio of 500/1 (by weight), and subjected to a reaction at 37° C. for 24 hours. After the termination of the reaction, the enzyme was inactivated through thermal treatment at 100° C. for 15 minutes, to recover a supernatant fraction by centrifugation. The pH of the supernatant fraction was neutralized with NaOH around neutrality, and the hydrolysate was recovered by freeze-drying. The free amino acids concurrently present in the hydrolysate were at 5% by weight or less.

Instead of the active rD3, alternatively, trypsin or alkalase was added to the casein solution preliminarily adjusted to optimum pH for each of trypsin and alkalase, to a final substrate/enzyme ratio of 500/1 (by weight), and subjected to a reaction at 37° C. for 24 hours. After the termination of the reaction, the hydrolysates were recovered by the same method. The free amino acids concurrently present in the hydrolysates were at 5% by weight or less.

The average molecular weights of the casein hydrolysates are shown in Table 3. The hydrolysate powders were dissolved in water to 1% by weight, to carry out the assessment of bitterness. As shown in Table 4, the casein hydrolysate from rD3 had significantly less bitterness than from the other enzymatic hydrolysates. Thus, the superiority of the hydrolysate by rD3 as a peptide material is shown.

TABLE 3

| Enzyme | Average molecular weight |
| --- | --- |
| rD3 | 1202 |
| Pepsin | 2096 |
| Alkalase | 795 |

TABLE 4

| Enzyme | Equivalent concentration (%) |
| --- | --- |
| rD3 | 0.020 |
| Pepsin | 0.053* |
| Alkalase | 0.073* |

*Significantly more bitter than the hydrolysate produced by rD3 at p < 0.05.

Having now fully described this invention, it will be apparent to one of ordinary skill in the art that many changes and modifications can be made thereto without departing from the spirit or scope of the invention as set forth herein.

What is claimed as new and desired to be secured by Letters Patent of the Uniter States is:

1. A method of making a product selected from the group consisting of foodstuffs, infant formula, medicinal diets, seasonings, flavor-modifying materials, food property-modifying materials, food additives, and feeds, comprising:

(A) contacting a protein with a thiol protease obtainable from germinating soybean iotyledons to produce a protein hydrolysate with a bitterness of 0.05% or less and a content of free amino acids of 5% or less, wherein the thiol protease has the following properties:

(1) molecular weight (SDS-PAGE): 26 to 30 kDa,
(2) optimum pH: about 3 to 7,
(3) optimum temperature: about 30 to 50° C., and
(4) inhibitors: trans-epoxysuccinyl-L-leucylamide(4-guanizino)-butane (E-64), and
(5) activators: 2-mercaptoethanol, cysteine, and reduced glutathione, and (B) incorporating the protein hydrolysate into the product.

2. The method of claim 1, wherein the protease has a specificity for cleaving C-terminals of hydrophilic amino acid residues adjacent to C-terminals of hydrophobic amino acid residues in the protein.

3. The method of claim 1, wherein the protease is D3.

4. The method of claim 1, wherein the hydrolysate contains peptides having a molecular range of from 200 to 8,000 Da.

5. The method of claim 1, wherein the hydrolysate contains peptides having a molecular range of from 200 to 5 000 Da.

6. The method of claim 1, wherein the hydrolysate contains peptides having a molecular range of from 200 to 2,000 Da.

7. The method of claim 1, wherein the protein is selected from the group consisting of vegetable proteins and animal proteins.

8. The method of claim 1, wherein the protein is selected from the group consisting of soybean protein, gluten, casein, gelatin, muscle protein, globulin, and albumin.

9. The method of claim 1, wherein the protein is a soybean protein.

10. The method of claim 1, wherein the hydrolysate has a bitterness of 0.04% or less.

11. The method of claim 1, wherein the hydrolysate has a bitterness of 0.02% or less.

12. The method of claim 1, wherein the product is a foodstuff.

13. The method of claim 1, wherein the product is as infant formula.

14. The method of claim 1, wherein the product is a medicinal diet.

15. The method of claim 1, wherein the product is a seasoning.

16. The method of claim 1, wherein the product is a flavor-modifying material.

17. The method of claim 1, wherein the product is a food property-modifying material.

18. The method of claim 1, wherein the product is a food additive.

19. The method of claim 1, wherein the product is a feed.

* * * * *

UNITED STATES PATENT AND TRADEMARK OFFICE
CERTIFICATE OF CORRECTION

PATENT NO. : 6,455,273 B1
DATED : September 24, 2002
INVENTOR(S) : Kodera et al.

It is certified that error appears in the above-identified patent and that said Letters Patent is hereby corrected as shown below:

<u>Title page,</u>
Item [75], the 3rd inventor's name should read:

-- [75] Inventors: Tomohiro Kodera; Minao Asano; Tetsuya Miwa; Noriki Nio, all of Kanagawa-ken (JP) --

Signed and Sealed this

Eleventh Day of February, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,455,273 B1
DATED : September 24, 2002
INVENTOR(S) : Kodera et al.

It is certified that error appears in the above-identified patent and that said Letters Patent is hereby corrected as shown below:

Column 1,
Line 64, delete "1g".

Column 4,
Line 18, "protein isolates." should read -- protein isolate --;
Line 44, "(his" should read -- this --;
Line 56, "hydrosylate" should read -- hydrolysate --.

Column 7,
Line 47, "Uniter" should read -- United --;
Line 53, "iotyledons" should read -- cotyledons --.

Column 8,
Line 20, "5 000" should read -- 5,000 --.

Signed and Sealed this

Twenty-sixth Day of August, 2003

JAMES E. ROGAN
*Director of the United States Patent and Trademark Office*